(12) United States Patent
Lin et al.

(10) Patent No.: US 7,736,861 B1
(45) Date of Patent: Jun. 15, 2010

(54) TIVOZANIB RESPONSE PREDICTION

(75) Inventors: Jie Lin, West Roxbury, MA (US); Bin Feng, N. Reading, MA (US); Murray Robinson, Boston, MA (US); Feng Jiang, Natick, MA (US); Xiaojian Sun, Cambridge, MA (US)

(73) Assignee: AVEO Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 12/645,355

(22) Filed: Dec. 22, 2009

Related U.S. Application Data

(60) Provisional application No. 61/253,036, filed on Oct. 19, 2009.

(51) Int. Cl.
*G01N 33/53* (2006.01)

(52) U.S. Cl. ........................................... 435/7.1

(58) Field of Classification Search ............... None
See application file for complete search history.

(56) References Cited

U.S. PATENT DOCUMENTS

2007/0264193 A1  11/2007  Shojaei et al.

OTHER PUBLICATIONS

Tockman et al (Cancer Res., 1992, 52:2711s-2718s).*
Hamada et al (Anticancer Research, 2002, 22:4281-4284).*
Shidham et al (The American Journal of Surgical Pathology, 2001, 25(8): 1039-1049).*
Hamada et al., "Clinical Effects of Tumor-associated Macrophages and Dendritic Cells on Renal Cell Carcinoma," *Anticancer Research*, vol. 22, pp. 4281-4284, 2002.
Kobayashi et al., "Tumor Infiltrating Dendritic Cells Predict Treatment Response to Immmunotherapy [sic] in Patients with Metastatic Renal Cell Carcinoma," *Anticancer Research*, vol. 27, pp. 1137-1141, 2007.
Murdoch et al., "The Role of Myeloid Cells in the Promotion of Tumour Angiogenesis," *Nature Reviews / Cancer*, Aug. 2008, vol. 8, pp. 618-631.
Shojaei et al., "G-CSF-initiated Myeloid Cell Mobilization and Angiogenesis Mediate Tumor Refractoriness to Anti-VEGF Therapy in Mouse Models," *PNAS*, Apr. 21, 2009, vol. 106, No. 16, pp. 6742-6747.
Shojaei et al., "Tumor Refractoriness to Anti-VEGF Treatment is Mediated by $CD11b^+Gr1^+$ Myeloid Cells," *Nature Biotechnology*, vol. 25, No. 8, Aug. 2007, pp. 911-920.

* cited by examiner

*Primary Examiner*—Sean E Aeder
(74) *Attorney, Agent, or Firm*—Gary L. Creason

(57) ABSTRACT

A diagnostic method for predicting whether a human tumor will be sensitive or resistant to treatment with tivozanib (AV-951) is disclosed. The method is based on measurement of macrophage content in a tissue sample from a tumor. Measurement of macrophage content can be based on analysis of macrophage marker gene expression, e.g., by RNA analysis or immunohistochemistry.

4 Claims, 4 Drawing Sheets

TIVOZANIB RESPONSE PREDICTION

CROSS-REFERENCE TO RELATED APPLICATIONS

This application claims the benefit of and priority to U.S. provisional patent application Ser. No. 61/253,036, filed Oct. 19, 2009; the entire contents of which are incorporated herein by reference.

FIELD OF THE INVENTION

The field of the invention is molecular biology, oncology, and clinical diagnostics.

BACKGROUND OF THE INVENTION

Most cancer drugs are effective in some patients, but not in others. This results from genetic variation among tumors, and can be observed even among tumors within the same patient. Variable patient response is particularly pronounced with respect to targeted therapeutics. Therefore, the full potential of targeted therapies cannot be realized without suitable tests for determining which patients will benefit from which drugs. According to the National Institutes of Health (NIH), the term "biomarker" is defined as "a characteristic that is objectively measured and evaluated as an indicator of normal biologic or pathogenic processes or pharmacological response to a therapeutic intervention."

The development of improved diagnostics based on the discovery of biomarkers has the potential to accelerate new drug development by identifying, in advance, those patients most likely to show a clinical response to a given drug. This would significantly reduce the size, length and cost of clinical trials. Technologies such as genomics, proteomics and molecular imaging currently enable rapid, sensitive and reliable detection of specific gene mutations, expression levels of particular genes, and other molecular biomarkers. In spite of the availability of various technologies for molecular characterization of tumors, the clinical utilization of cancer biomarkers remains largely unrealized because few cancer biomarkers have been discovered. For example, a recent review article states:

There is a critical need for expedited development of biomarkers and their use to improve diagnosis and treatment of cancer. (Cho, 2007, *Molecular Cancer* 6:25.)

Another recent review article on cancer biomarkers contains the following comments:

The challenge is discovering cancer biomarkers. Although there have been clinical successes in targeting molecularly defined subsets of several tumor types—such as chronic myeloid leukemia, gastrointestinal stromal tumor, lung cancer and glioblastoma multiforme—using molecularly targeted agents, the ability to apply such successes in a broader context is severely limited by the lack of an efficient strategy to evaluate targeted agents in patients. The problem mainly lies in the inability to select patients with molecularly defined cancers for clinical trials to evaluate these exciting new drugs. The solution requires biomarkers that reliably identify those patients who are most likely to benefit from a particular agent. (Sawyers, 2008, *Nature* 452:548-552, at 548.)

Comments such as the foregoing illustrate the recognition of a need for the discovery of clinically useful biomarkers and diagnostic methods based on such biomarkers.

There are three distinct types of cancer biomarkers: (1) prognostic biomarkers, (2) predictive biomarkers, and (3) pharmacodynamic (PD) biomarkers. A prognostic biomarker is used to classify a cancer, e.g., a solid tumor, according to aggressiveness, i.e., rate of growth and/or metastasis, and refractiveness to treatment. This is sometimes called distinguishing "good outcome" tumors from "poor outcome" tumors. A predictive biomarker is used to assess the probability that a particular patient will benefit from treatment with a particular drug. For example, patients with breast cancer in which the ERBB2 (HER2 or NEU) gene is amplified are likely to benefit from treatment with trastuzumab (HERCEPTIN®), whereas patients without ERBB2 gene amplification are unlikely to benefit from treatment with trastuzumab. A PD biomarker is an indication of the effect(s) of a drug on a patient while the patient is taking the drug. Accordingly, PD biomarkers often are used to guide dosage level and dosing frequency, during the early stages of clinical development of a new drug. For a discussion of cancer biomarkers, see, e.g., Sawyers, 2008, *Nature* 452:548-552.

Tivozanib (also known as AV-951) is a potent and selective small-molecule inhibitor of VEGF receptors 1, 2 and 3. Tivozanib exhibits picomolar inhibitory activity against all three receptors, and it exhibits antitumor activity in preclinical models (Nakamura et al., 2006, *Cancer Res.* 66:9134-9142). Tivozanib has yielded positive interim results in a 272-patient Phase 2 clinical trial (Bhargava et al., 2009, *ASCO Genitourinary Cancers Symposium*, Abstract No. 283).

Despite a large amount of pre-clinical and clinical research focused on VEGF-targeted therapy, the mechanisms responsible for the anti-tumor activity of anti-VEGF agents are not fully understood. As with other types of targeted therapy, some, but not all, patients benefit from tivozanib therapy. The complexity of VEGF biology makes the effectiveness of tivozanib against any given tumor unpredictable. Therefore, there is a need for diagnostic methods based on predictive biomarkers that can be used to identify patients with tumors that are likely (or unlikely) to respond to treatment with tivozanib.

SUMMARY OF THE INVENTION

The invention is based, in part, on the discovery that elevated macrophage content (e.g., elevated macrophage number or elevated expression of a macrophage marker, e.g., elevated expression of a macrophage marker protein or elevated expression of a mRNA encoding a macrophage marker protein) in a tissue sample from a mammalian tumor correlates with resistance to treatment with tivozanib. Accordingly, the invention provides a method of identifying a tumor that likely is resistant to treatment with tivozanib. The method includes: (a) measuring macrophage content in a tissue sample from the tumor, thereby determining a macrophage score; and (b) comparing the macrophage score against a threshold score defined by a threshold determination analysis. A macrophage score above the threshold score is indicative that the tumor is likely to be resistant to treatment with tivozanib. A macrophage score below the threshold score is indicative that the tumor is likely to be responsive to treatment with tivozanib.

In some embodiments of the invention, measuring macrophage content is performed by measuring the presence or an amount of a macrophage marker protein. In other embodiments, measuring macrophage content is performed by determining the number of macrophages in a given cell population. For example, measuring macrophage content can be performed by immunohistochemistry involving detection of a macrophage marker protein. In another embodiment, measuring macrophage content is performed by measuring the presence or an amount of mRNA encoding a macrophage marker protein. Examples of macrophage marker proteins include CCR2, CD14, CD68, CD163, CSF1R and MSR1. The threshold determination analysis can include a receiver operator characteristic curve analysis. Methods of the invention are useful for testing various types of tumors, including, e.g., breast tumors, lung tumors, kidney tumors, colorectal tumors, and pancreatic tumors.

DETAILED DESCRIPTION OF THE INVENTION

Definitions

Figure 1:
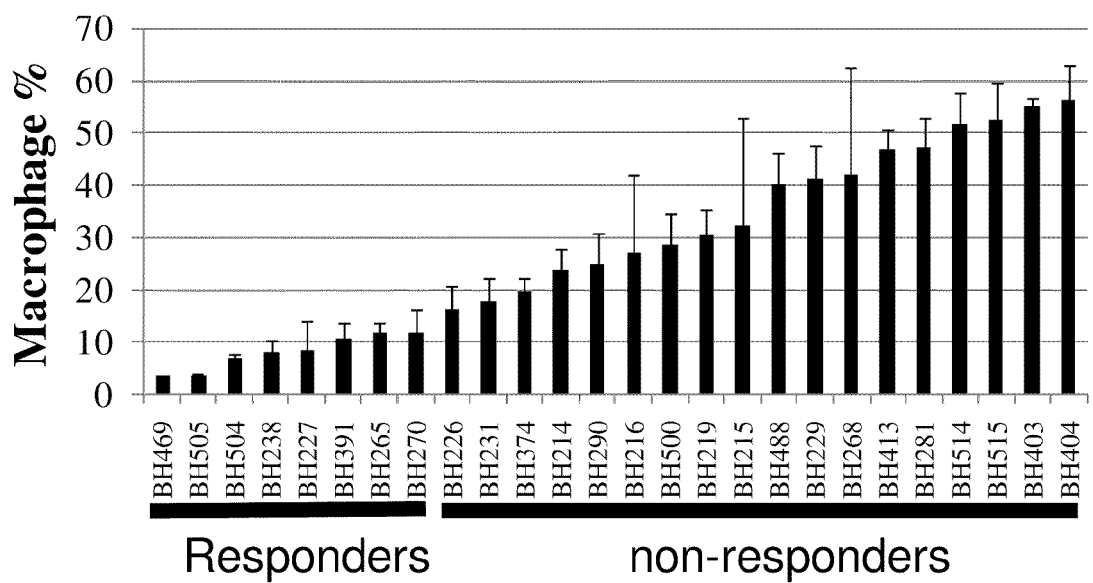
FIG. 1 is a bar graph showing the macrophage score (%) of 26 individual murine breast tumors, rank ordered by macrophage content, from lowest to highest. The first eight tumors (moving left to right) are classified as responsive to the treatment with tivozanib described in Example 1 (tivozanib sensitive tumors). The remaining 18 tumors are classified as non-responsive to the treatment with tivozanib described in Example 1 (tivozanib resistant tumors). Error bars indicate standard error (n=3). Macrophage score (%) was calculated as MSR1-positive cells or F4/80-positive cells (as determined by IHC) divided by the total number of cells times 100%.
Figure 2:
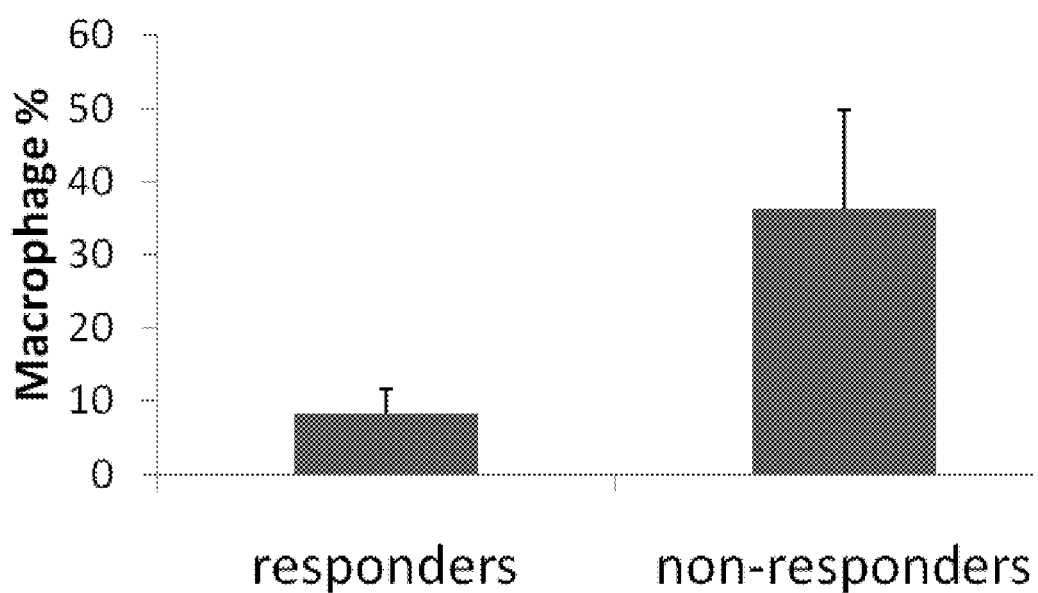
FIG. 2 is a bar graph showing the average macrophage score (percentage of the number of MSR-1 positive cells or F4/80-positive cells divided by the total number of cells in a given sample) of the tivozanib sensitive tumors in FIG. 1, and the tivozanib resistant tumors in FIG. 1. Average macrophage percentage in tivozanib sensitive tumors was found to be 8.2%±3.3%. Average macrophage percentage in tivozanib resistant tumors was found to be 36.4%±13.4%.

As used herein, "AV-951" and "tivozanib" mean N-{2-chloro-4-[(6,7-dimethoxy-4-quinolyl)oxy]-phenyl}-N'-(5-methyl-3-isoxazolyl)urea, which has the following chemical structure, including salts and polymorphs thereof:

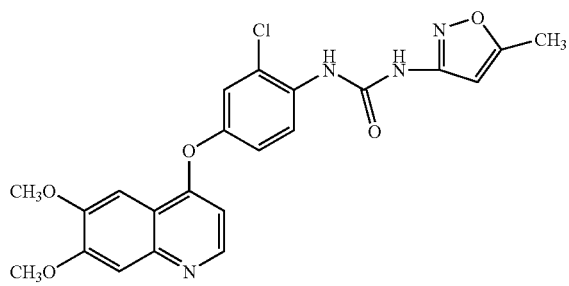

As used herein, "macrophage marker protein" means a macrophage cell surface protein, the detection of which is useful for identifying macrophages among the other types of cells present in a tissue sample from a tumor. Exemplary human macrophage marker proteins are CCR2, CD14, CD68, CD163, CSF1R and MSR1. Other macrophage marker proteins can be employed in practicing the present invention.

As used herein, "optimum threshold score" means the threshold score at which the classifier gives the most desirable balance between the cost of false negative calls and false positive calls.

As used herein, "receiver operating characteristic" (ROC) curve means a plot of false positive rate (sensitivity) versus true positive rate (specificity) for a binary classifier system. In construction of an ROC curve, the following definitions apply:

False negative rate "FNR"=1−TPR

True positive rate "TPR"=true positive/(true positive+false negative)

False positive rate "FPR"=false positive/(false positive+true negative)

As used herein, "response" or "responding" to treatment means, with regard to a treated tumor, that the tumor displays: (a) slowing of growth, (b) cessation of growth, or (c) regression.

As used herein, a "macrophage score" is a numerical value representing the level of macrophage content in a tumor. For example, in one embodiment, the macrophage score can be expressed as the number of macrophages in a given cell population, which can be expressed as a percentage, ratio, or otherwise. In other embodiments, the macrophage score can be expressed as a density, i.e., the number of macrophages in a unit volume in the tumor. In another embodiment, the macrophage score can be expressed as a level of expression of a macrophage marker protein or an mRNA encoding the macrophage marker protein. The level of protein expression can be obtained by, e.g., ELISA or other immunological methods. The gene expression level can be obtained by, e.g., qRT-PCR, microarray, or other analyses. The macrophage score can be interpreted with respect to a threshold score, which can be empirically determined in a threshold determination analysis, e.g., using ROC curve analysis.

As used herein, "threshold determination analysis" means analysis of a dataset representing a given tumor type, e.g., human renal cell carcinoma, to determine a threshold score for that particular tumor type. The dataset representing a given tumor type includes, for each tumor from a group of such tumors: (a) actual tumor response data (response and non-response to tivozanib), and (b) macrophage content.

As used herein, "threshold score" means a score above which a tumor is classified as being likely resistant to tivozanib treatment.

As used herein, "CCR2" (chemokine (C-C motif) receptor 2 also known as CD192, CKR2, CMKBR2, MCP-1-R, CC-CKR-2, FlJ78302, MGC103828, MGC111760, and MGC168006) means the human protein encoded by the gene identified by Entrez GeneID No. 729230 and allelic variants thereof.

As used herein, "CD14" means the human protein encoded by the gene identified by Entrez GeneID No. 929 and allelic variants thereof.

As used herein, "CD68" (also known as GP110; SCARD1; and DKFZp686M18236) means the human protein encoded by the gene identified by Entrez GeneID No. 968 and allelic variants thereof.

As used herein, "CD163" (also known as M130 and MM130) means the human protein encoded by the gene identified by Entrez GeneID No. 9332 and allelic variants thereof.

As used herein, "CSF1R" (colony stimulating factor 1 receptor also known as CSFR, FMS, FIM2, C-FMS, and CD115) means the human protein encoded by the gene identified by Entrez GeneID No. 1436 and allelic variants thereof.

As used herein, "MSR1" (macrophage scavenger receptor 1 also called CD204, SCARA1, SR-A, phSR1 and phSR2) means the human protein encoded by the gene identified by Entrez GeneID No. 4481 and allelic variants thereof.

As used herein "F4/80" (also known as EMR1, Ly71, GPF480, TM7LN3, DD7A5-7, EGF-TM7) means the murine protein encoded by the gene identified by Entrez GeneID No. 13733 and allelic variants thereof.

Tissue Sample

A tissue sample from a tumor in a human patient can be used as a source of RNA, a source of protein, or a source of thin sections for immunohistochemistry (IHC), so the level of macrophage content in the sample can be determined in practicing the present invention. The tissue sample can be obtained by using conventional tumor biopsy instruments and procedures. Endoscopic biopsy, excisional biopsy, incisional biopsy, fine needle biopsy, punch biopsy, shave biopsy and skin biopsy are examples of recognized medical procedures that can be used by one of skill in the art to obtain tumor samples. The tumor tissue sample should be large enough to provide sufficient RNA, protein, or thin sections for measuring marker gene, e.g., CD68, expression level or visualizing macrophages by IHC, e.g., CD68-positive cell expression.

The tumor tissue sample can be in any form that allows measurement of macrophage content. In other words, the tissue sample must be sufficient for RNA extraction, protein extraction, or preparation of thin sections. Accordingly, the tissue sample can be fresh, preserved through suitable cryogenic techniques, or preserved through non-cryogenic techniques. A standard process for handling clinical biopsy specimens is to fix the tissue sample in formalin and then embed it in paraffin. Samples in this form are commonly known as formalin-fixed, paraffin-embedded (FFPE) tissue. Suitable techniques of tissue preparation for subsequent analysis are well-known to those of skill in the art.

Macrophage Content

In practicing the present invention, determining the level of macrophage content (e.g., macrophage number or expression of a macrophage marker, e.g., expression of a macrophage marker protein or expression of a mRNA encoding a macrophage marker protein) in a tissue sample (e.g., from a tumor) can be performed by any suitable method, of which there are several. For example, measuring macrophage content indirectly can be done by measuring the expression of one or more genes known to be useful as macrophage markers. Various methods for measuring gene expression are known in the art. Such methods can be applied in determining the level of macrophage marker proteins or mRNA encoding macrophage marker proteins. Exemplary human macrophage marker genes are CCR2, CD14, CD68, CD163, CSF1R and MSR1. Other macrophage markers can be used, as well.

RNA Analysis

Conventional microarray analysis and quantitative polymerase chain reaction (QPCR) are examples of methods for determining the level of macrophage marker gene expression at the mRNA level. In some embodiments of the invention, RNA is extracted from the cells, tumor or tissue of interest using standard protocols. In other embodiments, RNA analysis is performed using techniques that do not require RNA isolation.

RNA Isolation

Methods for rapid and efficient extraction of eukaryotic mRNA, i.e., poly(a) RNA, from tissue samples are well established and known to those of skill in the art. See, e.g., Ausubel et al., 1997, *Current Protocols of Molecular Biology*, John Wiley & Sons. The tissue sample can be fresh, frozen or fixed paraffin-embedded (FFPE) samples such as clinical study tumor specimens. In general, RNA isolated from fresh or frozen tissue samples tends to be less fragmented than RNA from FFPE samples. FFPE samples of tumor material, however, are more readily available, and FFPE samples are suitable sources of RNA for use in methods of the present invention. For a discussion of FFPE samples as sources of RNA for gene expression profiling by RT-PCR, see, e.g., Clark-Langone et al., 2007, *BMC Genomics* 8:279. Also see, De Andrés et al., 1995, *Biotechniques* 18:42044; and Baker et al., U.S. Patent Application Publication No. 2005/0095634. The use of commercially available kits with vendor's instructions for RNA extraction and preparation is widespread and common. Commercial vendors of various RNA isolation products and complete kits include Qiagen (Valencia, Calif.), Invitrogen (Carlsbad, Calif.), Ambion (Austin, Tex.) and Exiqon (Woburn, Mass.).

In general, RNA isolation begins with tissue/cell disruption. During tissue/cell disruption it is desirable to minimize RNA degradation by RNases. One approach to limiting RNase activity during the RNA isolation process is to ensure that a denaturant is in contact with cellular contents as soon as the cells are disrupted. Another common practice is to include one or more proteases in the RNA isolation process. Optionally, fresh tissue samples are immersed in an RNA stabilization solution, at room temperature, as soon as they are collected. The stabilization solution rapidly permeates the cells, stabilizing the RNA for storage at 4° C., for subsequent isolation. One such stabilization solution is available commercially as RNAlater® (Ambion, Austin, Tex.).

In some protocols, total RNA is isolated from disrupted tumor material by cesium chloride density gradient centrifugation. In general, mRNA makes up approximately 1% to 5% of total cellular RNA. Immobilized Oligo(dT), e.g., oligo(dT) cellulose, is commonly used to separate mRNA from ribosomal RNA and transfer RNA. If stored after isolation, RNA must be stored in under RNase-free conditions. Methods for stable storage of isolated RNA are known in the art. Various commercial products for stable storage of RNA are available.

Microarray

The mRNA expression level of one or more genes encoding macrophage marker proteins can be measured using conventional DNA microarray expression profiling technology. A DNA microarray is a collection of specific DNA segments or probes affixed to a solid surface or substrate such as glass, plastic or silicon, with each specific DNA segment occupying a known location in the array. Hybridization with a sample of labeled RNA, usually under stringent hybridization conditions, allows detection and quantitation of RNA molecules corresponding to each probe in the array. After stringent washing to remove non-specifically bound sample material, the microarray is scanned by confocal laser microscopy or other suitable detection method. Modern commercial DNA microarrays, often known as DNA chips, typically contain tens of thousands of probes, and thus can measure expression of tens of thousands of genes simultaneously. Such microarrays can be used in practicing the present invention. Alternatively, custom chips containing as few probes as those needed to measure expression of one or more genes encoding macrophage marker proteins, plus necessary controls or standards, e.g., for data normalization, can be used in practicing the invention.

To facilitate data normalization, a two-color microarray reader can be used. In a two-color (two-channel) system, samples are labeled with a first fluorophore that emits at a first wavelength, while an RNA or cDNA standard is labeled with a second fluorophore that emits at a different wavelength. For example, Cy3 (570 nm) and Cy5 (670 nm) often are employed together in two-color microarray systems.

DNA microarray technology is well-developed, commercially available, and widely employed. Therefore, in performing methods of the invention, a person of ordinary skill in the art can use microarray technology to measure expression levels of genes encoding macrophage marker proteins without undue experimentation. DNA microarray chips, reagents (such as those for RNA or cDNA preparation, RNA or cDNA labeling, hybridization and washing solutions), instruments (such as microarray readers) and protocols are well known in the art and available from various commercial sources. Commercial vendors of microarray systems include Agilent Technologies (Santa Clara, Calif.) and Affymetrix (Santa Clara, Calif.), but other PCR systems can be used.

Quantitative RT-PCR

The level of mRNA representing individual genes encoding macrophage marker proteins can be measured using conventional quantitative reverse transcriptase polymerase chain reaction (qRT-PCR) technology. Advantages of qRT-PCR include sensitivity, flexibility, quantitative accuracy, and ability to discriminate between closely related mRNAs. Guidance concerning the processing of tissue samples for quantitative PCR is available from various sources, including manufacturers and vendors of commercial products for qRT-PCR (e.g., Qiagen (Valencia, Calif.) and Ambion (Austin, Tex.)). Instrument systems for automated performance of qRT-PCR are commercially available and used routinely in many laboratories. An example of a well-known commercial system is the Applied Biosystems 7900HT Fast Real-Time PCR System (Applied Biosystems, Foster City, Calif.).

Once isolated mRNA is isolated, the first step in gene expression profiling by RT-PCR is the reverse transcription of the mRNA template into cDNA, which is then exponentially amplified in a PCR reaction. Two commonly used reverse transcriptases are avilo myeloblastosis virus reverse transcriptase (AMV-RT) and Moloney murine leukemia virus reverse transcriptase (MMLV-RT). The reverse transcription reaction typically is primed with specific primers, random hexamers, or oligo(dT) primers. Suitable primers are commercially available, e.g., GeneAmp® RNA PCR kit (Perkin Elmer, Waltham, Mass.). The resulting cDNA product can be used as a template in the subsequent polymerase chain reaction.

The PCR step is carried out using a thermostable DNA-dependent DNA polymerase. The polymerase most commonly used in PCR systems is a *Thermus aquaticus* (Taq) polymerase. The selectivity of PCR results from the use of primers that are complementary to the DNA region targeted for amplification, i.e., regions of the cDNAs reverse transcribed from genes encoding macrophage marker proteins. Therefore, when qRT-PCR is employed in the present invention, primers specific to each marker gene are based on the cDNA sequence of the gene. Commercial technologies such as SYBR® green or TaqMan® (Applied Biosystems, Foster City, Calif.) can be used in accordance with the vendor's instructions. Messenger RNA levels can be normalized for differences in loading among samples by comparing the levels of housekeeping genes such as beta-actin or GAPDH. The level of mRNA expression can be expressed relative to any single control sample such as mRNA from normal, non-tumor tissue or cells. Alternatively, it can be expressed relative to mRNA from a pool of tumor samples, or tumor cell lines, or from a commercially available set of control mRNA.

Suitable primer sets for PCR analysis of expression levels of genes encoding macrophage marker proteins can be designed and synthesized by one of skill in the art, without undue experimentation. Alternatively, PCR primer sets for practicing the present invention can be purchased from commercial sources, e.g., Applied Biosystems. PCR primers preferably are about 17 to 25 nucleotides in length. Primers can be designed to have a particular melting temperature (Tm), using conventional algorithms for Tm estimation. Software for primer design and Tm estimation are available commercially, e.g., Primer Express™ (Applied Biosystems), and also are available on the internet, e.g., Primer3 (Massachusetts Institute of Technology). By applying established principles of PCR primer design, a large number of different primers can be used to measure the expression level of any given gene, including macrophage marker genes such as CD14, CD68, MSR1, CSFR1, CD163 and CCR2.

gNPA™

In some embodiments of the invention, RNA analysis is performed using a technology that does not involve RNA extraction or isolation. One such technology is quantitative nuclease protection assay, which is commercially available under the name gNPA™ (High Throughput Genomics, Inc., Tucson, Ariz.). This technology can be advantageous when the tumor tissue samples to be analyzed are in the form of FFPE material. See, e.g., Roberts et al., 2007, *Laboratory Investigation* 87:979-997.

Protein Analysis

In methods of the invention, macrophage marker gene expression can be detected at the protein level. Examples of methods for measuring the level of macrophage marker gene expression at the protein level include enzyme linked immunosorbent assay (ELISA) and IHC analysis.

ELISA

Performing a macrophage marker protein ELISA, e.g., CD68 ELISA, requires at least one antibody against a macrophage marker protein, i.e., the detection antibody. In an exemplary embodiment, CD68 is the macrophage marker protein. CD68 protein from a sample to be analyzed is immobilized on a solid support such as a polystyrene microtiter plate. This immobilization can be by non-specific binding of the CD68, e.g., through adsorption to the surface. Alternatively, immobilization can be by specific binding, e.g., through binding of CD68 protein from the sample by a capture antibody (anti-CD68 antibody different from the detection antibody), in a "sandwich" ELISA. After the CD68 is immobilized, the detection antibody is added, and the detection antibody forms a complex with the bound CD68. The detection antibody is linked to an enzyme, either directly or indirectly, e.g., through a secondary antibody that specifically recognizes the detection antibody. Typically between each step, the plate, with bound CD68, is washed with a mild detergent solution. Typical ELISA protocols also include one or more blocking steps, which involve use of a non-specifically-binding protein such as bovine serum albumin to block unwanted non-specific binding of protein reagents to the plate. After a final wash step, the plate is developed by addition of an appropriate enzyme substrate, to produce a visible signal, which indicates the quantity of CD68 in the sample.

The substrate can be, e.g., a chromogenic substrate or a fluorogenic substrate. ELISA methods, reagents and equipment are well-known in the art and commercially available.

It is understood that the expression levels of other macrophage marker proteins, e.g., CCR2, CD14, CD163, CSF1R, and MSR1, as well as other macrophage specific marker proteins can be measured by ELISA using detecting antibodies specific for each macrophage marker protein.

Immunohistochemistry (IHC)

The number of macrophages in a given cell population can be determined (e.g., visualized) by immunohistochemistry. Assaying a macrophage marker protein by IHC, e.g., CD68 IHC, requires at least one antibody against a macrophage marker protein, e.g., at least one anti-CD68 antibody. Numerous anti-CD68 antibodies suitable for IHC are commercially available. For example, suitable antibodies can be purchased from Dako North America, Inc. (Carpinteria, Calif.), abcam (Cambridge, Mass.), Abnova (Walnut, Calif.), R&D Systems (Minneapolis, Minn.) or Invitrogen (Carlsbad, Calif.). Using standard techniques, the anti-CD68 antibody can be used to detect the presence of CD68 protein in sections, e.g., 5 micron sections, obtained from tumors, including paraffin-embedded and frozen tumor sections. Typically, the tumor sections are initially treated in such a way as to retrieve the antigenic structure of proteins that were fixed in the initial process of collecting and preserving the tumor material. Slides are then blocked to prevent non-specific binding by the anti-CD68 detection antibody. The presence of CD68 protein is then detected by binding of the anti-CD68 antibody to the CD68 protein. The detection (primary) antibody is linked to an enzyme, either directly or indirectly, e.g., through a secondary antibody or polymer that specifically recognizes the detection (primary) antibody. Typically, the tumor sections are washed and blocked with non-specific protein such as bovine serum albumin between steps. The slide is developed using an appropriate enzyme substrate to produce a visible signal. The samples can be counterstained with hematoxylin.

It is understood that the expression of other macrophage marker proteins, e.g., CCR2, CD14, CD163, CSF1R, and MSR1, as well as other macrophage specific marker proteins can be detected by IHC using antibodies specific for each macrophage marker protein.

Data Interpretation

A macrophage score for a tumor can be interpreted with respect to a threshold score. A macrophage score that is equal to or higher than the threshold score can be interpreted as predictive of the tumor being likely to be resistant (non-responsive) to tivozanib treatment. Alternatively, macrophage scores equal to or lower than the threshold score can be interpreted as predictive of a tumor being likely to be sensitive (responsive) to tivozanib treatment. For example, as shown in Example 2, the threshold score, which was calculated as the percentage of MSR1-positive cells or F4/80-positive cells (as determined by IHC) divided by the total number of cells is about 10% to about 15%.

An optimum threshold macrophage score can be determined (or at least approximated) empirically by performing a threshold determination analysis. Preferably, threshold determination analysis includes receiver operator characteristic (ROC) curve analysis. ROC curve analysis is an established statistical technique, the application of which is within ordinary skill in the art. For a discussion of ROC curve analysis, see generally Zweig et al., 1993, "Receiver operating characteristic (ROC) plots: a fundamental evaluation tool in clinical medicine," *Clin. Chem.* 39:561-577; and Pepe, 2003, *The statistical evaluation of medical tests for classification and prediction*, Oxford Press, New York.

Macrophage scores and the optimum threshold macrophage score may vary from tumor type to tumor type. Therefore, a threshold determination analysis preferably is performed on one or more datasets representing any given tumor type to be tested using the present invention. The dataset used for threshold determination analysis includes: (a) actual response data (response or non-response), and (b) a macrophage score for each tumor sample from a group of tumors. Once a macrophage score threshold is determined with respect to a given tumor type, that threshold can be applied to interpret macrophage scores from tumors of that tumor type.

The ROC curve analysis can be performed as follows. Any sample with a macrophage score greater than or equal to the threshold is identified as a non-responder (resistant). Alternatively, any sample with a macrophage score less than or equal to the threshold is identified as responder (sensitive). For every macrophage score from a tested set of samples, "responders" and "non-responders" (hypothetical calls) are classified using that score as the threshold. This process enables calculation of TPR (y vector) and FPR (x vector) for each potential threshold, through comparison of hypothetical calls against the actual response data for the data set. Then an ROC curve is constructed by making a dot plot, using the TPR vector, and FPR vector. If the ROC curve is above the diagonal from (0, 0) point to (1.0, 0.5) point, it shows that the macrophage test result is a better test than random.

The ROC curve can be used to identify the best operating point. The best operating point is the one that yields the best balance between the cost of false positives weighed against the cost of false negatives. These costs need not be equal. The average expected cost of classification at point x,y in the ROC space is determined by the following formula.

$$C=(1-p)\text{alpha}*x+p*\text{beta}(1-y)$$

wherein:
alpha=cost of a false positive,
beta=cost of missing a positive (false negative), and
p=proportion of positive cases.

False positives and false negatives can be weighted differently by assigning different values for alpha and beta. For example, if it is decided to include more patients in the responder group at the cost of treating more patients who are non-responders, one can put more weight on alpha. In this case, it is assumed that the cost of false positive and false negative is the same (alpha equals to beta). Therefore, the average expected cost of classification at point x,y in the ROC space is:

$$C'=(1-p)*x+p*(1-y).$$

The smallest C' can be calculated after using all pairs of false positive and false negative (x, y). The optimum score threshold is calculated as the score of the (x, y) at C'.

In addition to predicting whether a tumor will be sensitive or resistant to tivozanib treatment, i.e., binary classification, a macrophage score provides an approximate, but useful, indication of how likely a tumor is to be sensitive or resistant. In general, the lower the macrophage score, the more likely a tumor is to be sensitive to tivozanib, and the higher the macrophage score, the more likely a tumor is to be resistant to tivozanib.

Test Kits

The invention includes a diagnostic test kit comprising certain components for performing methods of the invention. A diagnostic test kit enhances convenience, speed and reproducibility in the performance of diagnostic assays. For example, in an exemplary qRT-PCR-based embodiment of the invention, a basic diagnostic test kit includes PCR primers for analyzing expression of macrophage markers, e.g., CD68. In other embodiments, a more elaborate test kit contains not only PCR primers, but also buffers, reagents and detailed instructions for measuring CD68 expression levels, using PCR technology. In some embodiments, the kit includes a test protocol and all the consumable components needed for the test, except the RNA sample(s).

In an exemplary DNA microarray-based embodiment of the invention, a test kit includes a micro fluidic card (array) designed for use with a particular instrument. Optionally, the micro fluidic card is a custom made device designed specifically for measurement of macrophage marker gene expression. Such custom micro fluidic cards are commercially available. For example, the TaqMan Array is a 384-well micro fluidic card (array) designed for use with the Applied Biosystems 7900HT Fast Real Time PCR System (Applied Biosystems, Foster City, Calif.). An exemplary fluidic card may include any combination of probes for measuring CCR2, CD14, CD68, CD163, CSF1R and/or MSR1 expression plus necessary controls or standards, e.g., for data normalization. Other macrophage marker proteins can also be included on a fluidic card for practicing the invention.

In some embodiments of the invention, the test kit contains materials for determining tumor macrophage content by IHC. An IHC kit, for example, may contain a primary antibody against a human macrophage marker, e.g., a mouse anti-human CD68 antibody, and a secondary antibody conjugated to a reporter enzyme, e.g., horseradish peroxidase. In some embodiments, the secondary antibody is replaced with a conjugated polymer that specifically recognizes the primary antibody.

EXAMPLES

The invention is further illustrated by the following examples. The examples are provided for illustrative purposes only, and are not to be construed as limiting the scope or content of the invention in any way.

Example 1

Murine Tumor Response to Tivozanib

A library of more than 100 murine breast tumors (BH archive) was used to identify tumors that are sensitive to tivozanib (responders) and tumors that are resistant to tivozanib (non-responders). The BH archive was established by in vivo propagation and cryopreservation of primary tumor material from more than 100 spontaneous murine breast tumors derived from engineered chimeric mice that develop Her2-dependent, inducible spontaneous breast tumors. The mice were produced essentially as follows.

Ink4a homozygous null ES cells were co-transfected with the following four constructs, as separate fragments: MMTV-rtTA, TetO-Her2$^{V664Eneu}$, TetO-luciferase and PGK-puromycin. Puromycin-resistant cells were genotyped by PCR and Southern blot. Inducibility of the oncogenes in ES cells was analyzed by northern blot. The transfected ES cells were injected into C57BL/6 blastocysts, which were transplanted into pseudo-pregnant female mice for gestation leading to birth of the chimeric mice.

The mouse mammary tumor virus long terminal repeat (MMTV) was used to drive breast-specific expression of the reverse tetracycline transactivator (rtTA). The rtTA provided for breast-specific expression of the Her2 activated oncogene, when doxycycline was provided to the mice in their drinking water.

Inducibility of the Her2 oncogene and luciferase was confirmed by RT-PCR and luciferase assay, respectively, using cultured cells derived from the mouse. Mammary glands were removed from chimeric mice and digested with collagenase. Half of the organoids collected were cultured in the presence of doxycycline, and the other half was cultured without doxycycline. After five days in culture, the cells were trypsinized, and one tenth of the cells were used for luciferase assay, and the rest were used for RNA extraction.

The histology analysis of tumors harvested from Her2 breast cancer model mice showed invasive adenocarcinomas. Two major patterns were distinguished. They were a solid sheet growth pattern, and a nested growth pattern with necrotic centers. Immunohistochemistry analysis of the mammary tumors revealed two cell types within the tumors. The first cell type was epithelial origin (cytokeratin positive), and showed Her2 expression and strong proliferation. The second cell type was mesenchymal origin with fibroblast-like appearance. These cells were collagen positive, did not show strong proliferation, and displayed stromal function. Apoptosis was seen in the necrotic centers of the epithelial part of the tumors. Tumor regression studies (regression in response to withdrawal of doxycycline) were performed to confirm that the murine model tumors were dependent on Her2 expression. Following induction of the tetracycline-responsive promoter by doxycycline, the mice developed mammary tumors with a latency of about 2 to 4 months.

Tumor cells were isolated by physical disruption of the tumors using cell strainers. Typically $1 \times 10^5$ cells were mixed with matrigel (50:50 volume) and injected subcutaneously into female NCr nu/nu mice on upper dorsal region between the shoulder blades. When these tumors grew to approximately 500 mm$^3$, which typically required 2 to 4 weeks, they were collected for further propagation, drug response testing, and analysis. Analysis included microarray profiling, general histopathology, and IHC (CD31 for tumor vasculature, Ki67 for tumor cell proliferation). The characterization of this tumor population revealed a remarkable degree of variation in key parameters of angiogenesis such as microvasculature, VEGF expression and specific gene expression profiles.

Evaluation of tumor response to tivozanib was performed essentially as follows. Subcutaneously transplanted tumors were established by injecting physically disrupted tumor cells (mixed with Matrigel) into 7 week-old female NCr nude mice. When the tumors reached approximately 200-400 mm$^3$, 30 tumor-bearing mice were randomized into three groups. Group 1 received vehicle. Group 2 received tivozanib at 5 mg/kg daily by oral gavage. Group 3 received tivozanib at 20 mg/kg daily by oral gavage. Tumors were measured twice per week by a caliper, and tumor volume was calculated. At the end of the treatment, tumors were collected for histopathological analysis and IHC analysis.

These studies revealed significant tumor-to-tumor variation in response to tivozanib. Based on tumor growth inhibition and typical histopathological and IHC (CD31) characteristics for angiogenesis inhibition, responders and non-responders were identified. Typically, responders exhibited (by histology) no tumor progression by caliper measurement and close to complete tumor killing, except the peripheries, when treated with 5 mg/kg tivozanib. The variation in response was expected, because the mouse model tumors had arisen spontaneously, and therefore they were expected to contain differing sets of random mutations that had led to tumorigenesis, including tumor angiogenesis. Such variation in response was desirable, because it was similar to the variation in naturally occurring human tumors, and thus enabled identification of tivozanib-responsive tumors and tivozanib-resistant tumors for use in identifying the molecular signature or tivozanib responsiveness.

Example 2

Macrophage Content in Murine Breast Tumors

Tissue samples (approx. 1000 mm$^3$) from the panel of murine breast tumors described in Example 1 (above) were resected and fixed in formalin overnight. The fixed tumors were then parafinized for conventional IHC analysis to determine macrophage content of each tumor. Macrophages were identified by using MSR1 or F4/80 as macrophage cell surface markers. For MSR1 IHC, a rat anti-mouse MSR1 antibody (Dako North America, Inc., Carpinteria, Calif.) was incubated with 5 micron paraffin sections. The signal was detected by using a commercial rat-on-mouse HRP-polymer detection kit (Biocare Medical, LLC, Concord, Calif., Catalog No. RT517) in accordance with the vendor's instructions. For F4/80 IHC, a rat anti-mouse F4/80 antibody (Serotec, MCA497R) was used on consecutive sections. The F4/80 signal was detected using the same rat-on-mouse HRP-polymer detection kit.

Macrophages identified by positivity in the MSR1 assay or F4/80 assay were counted by projecting a high power microscope field (200×) onto a touch sensitive pad image analyzer. For each breast tumor, three biological replicas (n=3 sc tumors from the same study) were analyzed with five fields from the sections, across the center of the tumor. Macrophage score as a percentage was calculated as MSR1-positive cells or F4/80-positive cells divided by total cells times 100%. The results were expressed as an average of the 15 images, on a tumor-by-tumor basis. The results in terms of macrophage score (%), for tumors responsive to tivozanib and tumors not responsive to tivozanib are presented in FIG. 1.

Figure 3:
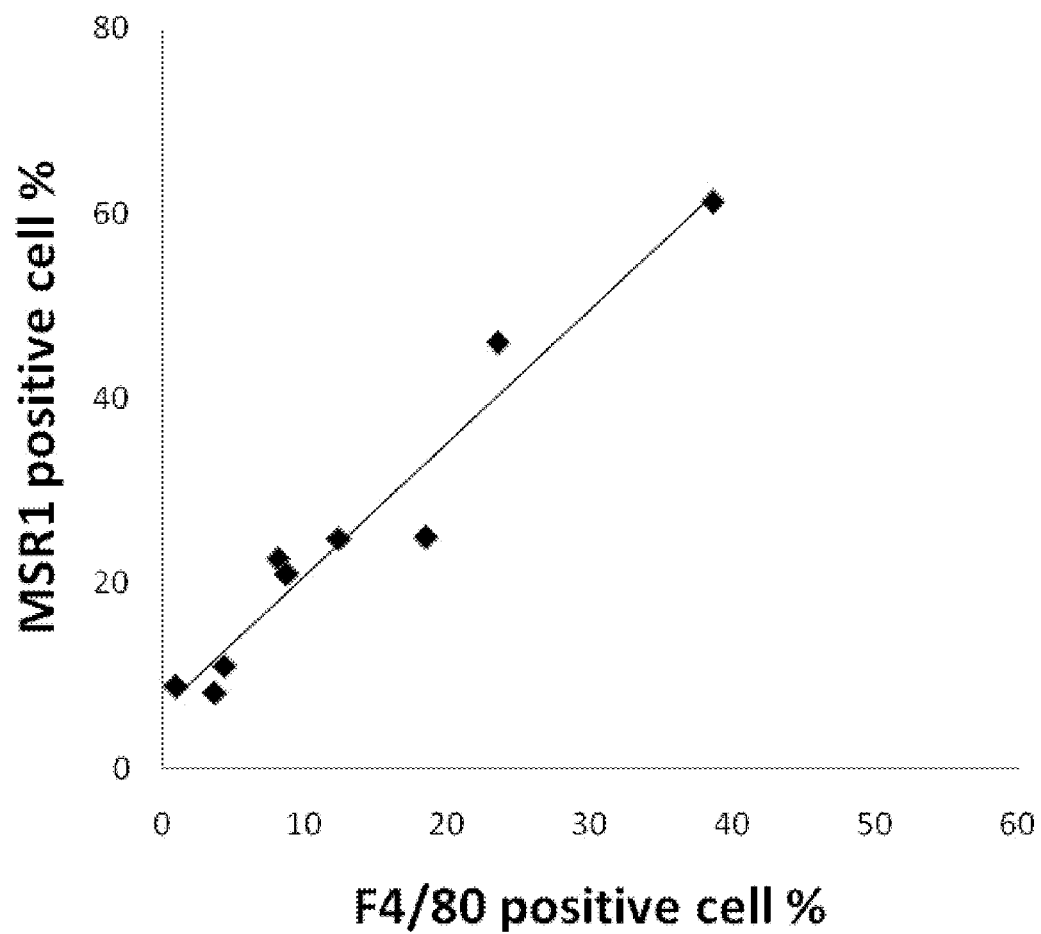
FIG. 3 is a plot of a linear regression (y=1.439 x+6.468) showing a high correlation between the number of MSR1-positive cells and the number of F4/80-positive cells ($R^2$=0.944), when consecutive sections of murine breast tumors were analyzed by IHC.

Assuming that MSR1 and F4/80 were functioning as reliable markers of macrophages in these sections, it was expected that the two markers would yield similar results. As an experimental control, this was confirmed by correlation analysis, which yielded a positive correlation of R2=0.944 (FIG. 3).

Example 3

Human Tumor Response to Tivozanib

When available, archival tumor tissue, from prior nephrectomy or biopsy, was collected from human patients enrolled in a Phase 2 clinical trial (AV-951-07-201 study). Patients enrolled in this study were required: (a) to have histologically or cytologically confirmed recurrent or metastatic renal cell carcinoma or primary renal cell carcinoma (RCC) (all histologies), (b) to have received no more than one prior systemic treatment for RCC; and (c) to have received no prior VEGF-targeted therapies. One hematoxylin and eosin slide, and up to four unstained slides and were collected, according to the local procedure, after informed consent was obtained.

This study was a phase 2, randomized, placebo-controlled, multicenter, discontinuation study designed to evaluate the safety, progression-free survival, anti-neoplastic activity, pharmacokinetic/pharmacodynamic, and pharmacogenomic/metabolomics of 1.5 mg tivozanib. All 272 patients enrolled in the study received open-label tivozanib, for the first 16-weeks. Patients received 1.5 mg/day of tivozanib continuously for 3 weeks followed by 1 week off study drug (1 cycle=3 weeks on, 1 week off). Patients were allowed dose reduction to 1.0 mg if they were unable to tolerate the 1.5 mg dose. Patients underwent disease assessment following every two treatment cycles. Response was be determined by Response Evaluation Criteria in Solid Tumors (RECIST) criteria (Version 1.0). After 16 weeks, patients with >25% tumor regression continued treatment with open-label tivozanib, while patients with <25% change (growth or shrinkage) from baseline were randomized to tivozanib or placebo, in a double-blind manner for the next 12 weeks. Patients with >25% increase in tumor size were removed from the study. The tumor tissue used in the analysis came from patients who had tumor tissue available at baseline and had undergone at least one tumor assessment following start of therapy. Furthermore, patients randomized to the placebo arm were not included in this sample analysis.

Example 4

Macrophage Content in Human RCC Tumors

Macrophage content in 21 human RCC tumors from the clinical study described in Example 3 (above) was measured in 5 micron sections from formalin fixed, paraffin embedded tumor tissue samples. The primary antibody for detecting human macrophages was a mouse anti-human CD68 antibody (Dako, Catalog No. m0814). The primary antibody was visualized by using a commercial mouse-on-human HRP-polymer detection kit (Biocare Medical, Catalog No. MHRP520), in accordance with the vendor's instructions.

Figure 4:
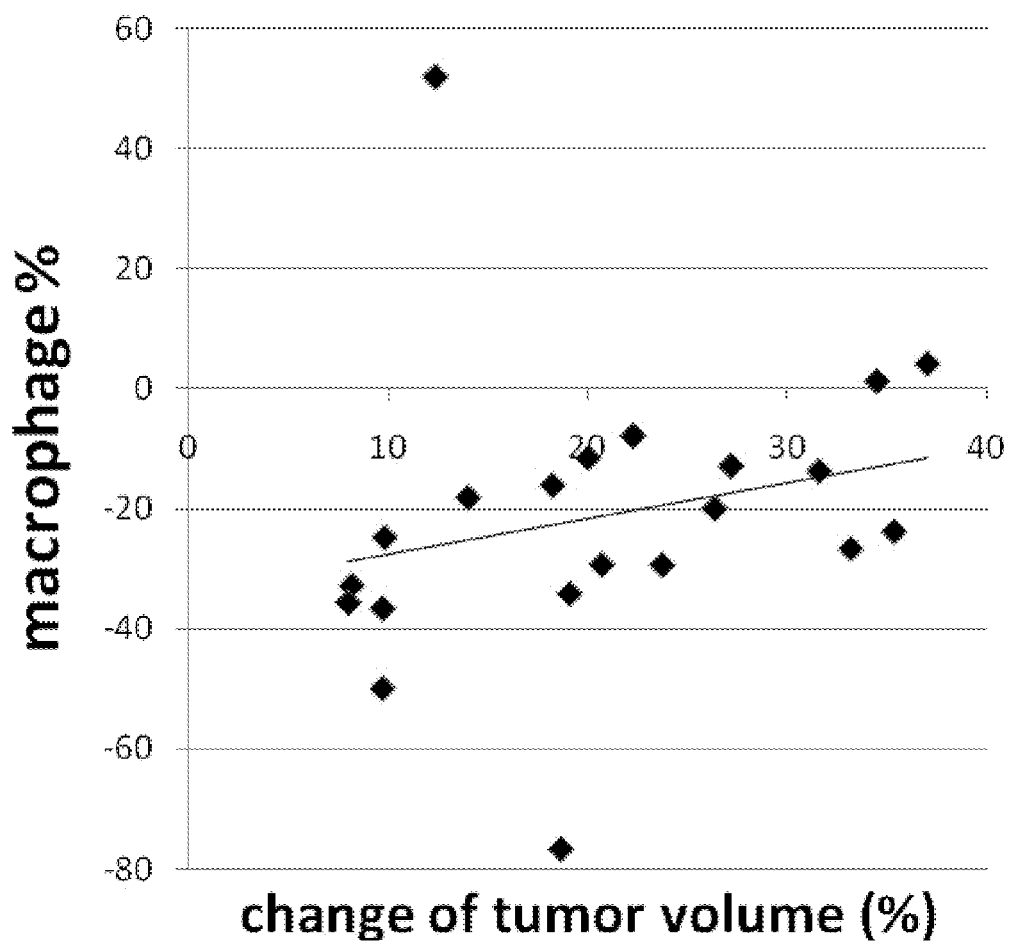
FIG. 4 is a scatter plot illustrating a linear regression trend line. Linear regression analysis indicates a high degree of correlation between macrophage content measured by CD68 IHC, and response of human renal cell carcinomas to treatment with tivozanib. Among 21 patients tested, the Rho value was 0.52, with p=0.017 (Spearman Correlation). This indicates that the greater the number of cells visualized as expressing the CD68 cell marker, the greater the resistance of the tumor to tivozanib. Solid line indicates linear regression.

Macrophages identified by positivity in the CD68 assay were counted by projecting a high power microscope field (200×) onto a touch sensitive pad image analyzer. For each tumor, one section was analyzed with five randomly-selected microscope fields. Macrophage score as percentage was calculated as CD68 positive cells divided by total cells multiplied by 100. A significant correlation between macrophage content of human tumors and resistance of the tumors to treatment with tivozanib was found. More specifically, the higher the macrophage number expressing CD68 in a tumor, the greater the resistance of the tumor to tivozanib. The results are summarized in a scatter plot of macrophage score (%) versus tumor response to tivozanib (FIG. 4). This result demonstrated that resistance of a human tumor to tivozanib treatment can be predicted by measurement of the macrophage content of the tumor.

INCORPORATION BY REFERENCE

The entire disclosure of each of the patent documents and scientific articles cited herein is incorporated by reference for all purposes.

EQUIVALENTS

The invention can be embodied in other specific forms with departing from the essential characteristics thereof. The foregoing embodiments therefore are to be considered illustrative rather than limiting on the invention described herein. The scope of the invention is indicated by the appended claims rather than by the foregoing description, and all changes that come within the meaning and range of equivalency of the claims are intended to be embraced therein.

What is claimed is:

1. A method of identifying a tumor resistant to treatment with tivozanib, comprising:
    (a) measuring macrophage content by measuring CD68 polypeptide expression in a tissue sample from a tumor obtained from a human patient being considered for treatment with tivozanib, thereby determining a macrophage score; and
    (b) comparing the macrophage score measured in step (a) against a threshold score determined by measuring CD68 polypeptide expression in tissue samples of tumors obtained from human patients previously treated with tivozanib and shown to be resistant to tivozanib and human patients previously treated with tivozanib and shown to be sensitive to tivozanib,
    wherein a macrophage score above the threshold score indicates that the tumor is resistant to treatment with tivozanib.

2. The method of claim 1, wherein the step of measuring CD68 polypeptide expression is performed by immunohistochemistry.

3. The method of claim 1, wherein the threshold score determination comprises a receiver operator characteristic curve analysis.

4. The method of claim 1, wherein the tumor is selected from the group consisting of a breast tumor, a lung tumor, a kidney tumor, a colorectal tumor, and a pancreatic tumor.

* * * * *